(12) United States Patent
Fried et al.

(10) Patent No.: US 8,239,031 B2
(45) Date of Patent: Aug. 7, 2012

(54) MIMICKING NEURAL CODING IN RETINAL GANGLION CELLS WITH SHORT PULSE ELECTRICAL STIMULATION

(75) Inventors: Shelley Fried, Berkeley, CA (US);
Frank Werblin, Berkeley, CA (US);
Matthew J. McMahon, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 506 days.

(21) Appl. No.: 11/506,388

(22) Filed: Aug. 17, 2006

(65) Prior Publication Data

US 2006/0282129 A1  Dec. 14, 2006

Related U.S. Application Data

(62) Division of application No. 11/293,331, filed on Dec. 1, 2005, now Pat. No. 8,103,352.

(60) Provisional application No. 60/675,981, filed on Apr. 28, 2005, provisional application No. 60/661,283, filed on Mar. 11, 2005, provisional application No. 60/632,929, filed on Dec. 3, 2004.

(51) Int. Cl.
*A61N 1/04* (2006.01)

(52) U.S. Cl. ............ 607/54; 607/2; 607/115; 607/116; 607/141

(58) Field of Classification Search ................ 607/2, 54, 607/115–116, 141
See application file for complete search history.

(56) References Cited

U.S. PATENT DOCUMENTS

| | | | |
|---|---|---|---|
| 3,628,193 A * | 12/1971 | Collins | 623/24 |
| 5,109,844 A | 5/1992 | de Juan, Jr. et al. | |
| 5,935,155 A | 8/1999 | Humayun et al. | |
| 5,944,747 A | 8/1999 | Greenberg et al. | |
| 6,400,989 B1 | 6/2002 | Eckmiller | |
| 6,442,431 B1 * | 8/2002 | Veraart et al. | 607/54 |
| 6,507,758 B1 | 1/2003 | Greenberg et al. | |
| 6,533,798 B2 | 3/2003 | Greenberg et al. | |
| 2002/0010496 A1 | 1/2002 | Greenberg et al. | |
| 2003/0139784 A1 * | 7/2003 | Morimoto et al. | 607/54 |

* cited by examiner

*Primary Examiner* — Carl H Layno
*Assistant Examiner* — Deborah Malamud
(74) *Attorney, Agent, or Firm* — Scott B. Dunbar; Alessandro Steinfl; Michael Chen

(57) ABSTRACT

A method, device and system for stimulating visual tissue, typically in the retina or visual cortex, to achieve an artificial percept of light or image. The method includes providing stimulating electrodes suitable for placement in proximity to the visual tissue and generating a series of short-duration stimulation signals having a duration of less than about 0.5 milliseconds each. The short-duration stimulation signals are applied through the stimulating electrodes with varying frequencies that are substantially matched to a spiking range of frequencies of at least one ganglion cell for perceiving brightness or image.

8 Claims, 9 Drawing Sheets

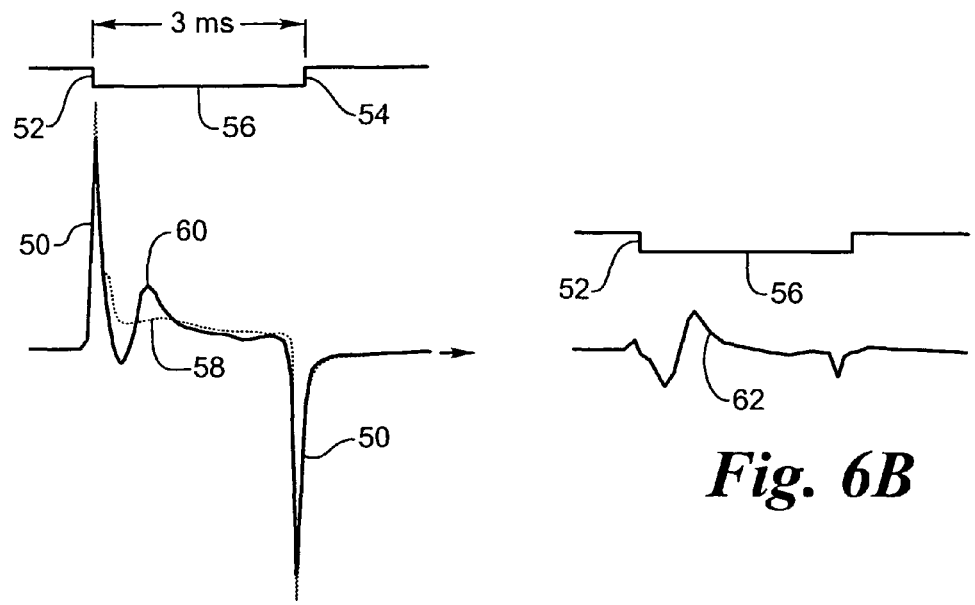
*Fig. 6A*
*Fig. 6B*
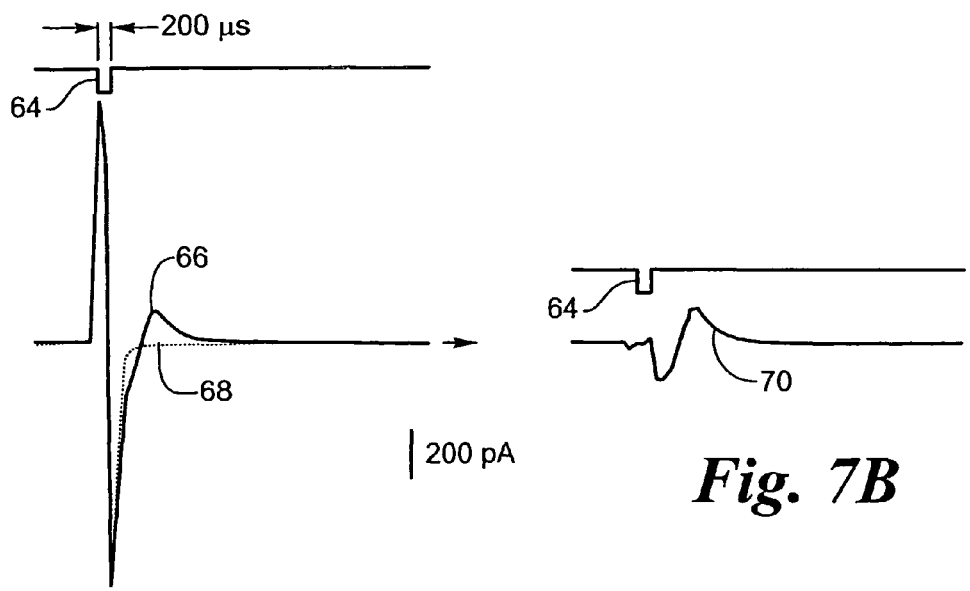
*Fig. 7A*
*Fig. 7B*

MIMICKING NEURAL CODING IN RETINAL GANGLION CELLS WITH SHORT PULSE ELECTRICAL STIMULATION

CROSS-REFERENCE TO RELATED APPLICATIONS

This patent application is a divisional application of U.S. patent application Ser. No. 11/293,331, filed Dec. 1, 2005 now U.S. Pat. No. 8,103,352 which claims benefit of the U.S. Provisional Patent Application Nos. 60/675,981 filed on Apr. 28, 2005, entitled Mimicking Neural Coding in Retinal Ganglion Cells with Short Pulse Electrical Stimulation; 60/661,283 filed on Mar. 11, 2005, entitled A Stimulus Paradigm for Precise Temporal Control of Retinal Spiking Elicited by Prosthetic Devices; and 60/632,929 filed on Dec. 3, 2004, entitled Mimicking Neural Coding in Retinal Ganglion Cells with Short Pulse Electrical Stimulation. The provisional patent applications are incorporated herein by reference, in their entirety, for all purposes.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to control of repetitive neural spikes and further to control perceived brightness by mimicking neural coding in a visual prosthesis.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation to small groups of individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 .mu.A current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Normann describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe.

Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

Retinal prosthetics use electricity to stimulate nerve cells. To be effective, the pattern of electrical stimulation should produce signals in the ganglion cells that mimic the signals they would receive under normal conditions. A major problem in mimicking normal neural activity is how to encode light intensity or brightness. Spiking neurons encode information in trains of action potentials, and it is generally accepted that most of the information about the intensity/brightness of the stimulus is encoded in the rate of action potentials provided to the brain through the optical nerve. Thus, there is a need to provide a method and apparatus to preferentially directly stimulate the ganglion cells with rate-coded intensity information.

BRIEF DESCRIPTION OF THE DRAWINGS

FIG. 6A is an illustration of a typical spiking response to a long-pulse electrical stimulation FIG. 6B is an illustration of a ganglion cell spike response generated by the long-pulse electrical stimulation shown in FIG. 6A, after subtracting the stimulus artifact.

FIG. 7A is an illustration of a ganglion cell response when stimulated by a short-pulse stimulation.

FIG. 7B is an illustration of a spike response elicited from a ganglion cell when stimulated by a short-pulse electrical stimulation.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
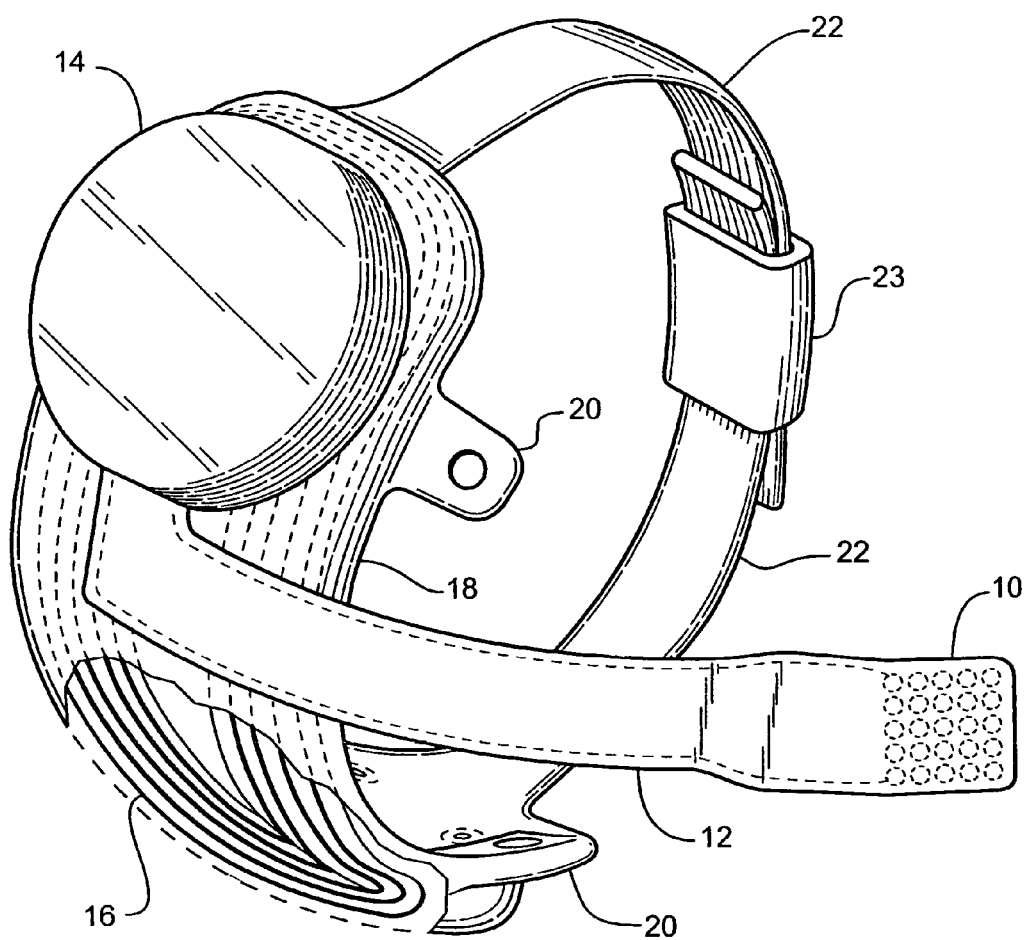
FIG. 1 is an illustration of a perspective view of an implantable portion of a visual prosthesis in accordance with an embodiment of the present invention.

FIG. 1 is an illustration of a perspective view of an implantable portion of a visual prosthesis in accordance with an embodiment of the present invention. An electrode array 10 is mountable by a retinal tack or similar means to the epiretinal surface. The electrode array 10 is electrically coupled by a cable 12 which pierces the sclera and is electrically coupled to an electronics package 14, external to the sclera.

The electronics package 14 is electrically coupled to an inductive coil 16. Preferably the inductive coil 16 is made from wound wire. Alternatively, the inductive coil may be made from a thin film polymer sandwich with wire traces deposited between layers of thin film polymer. The electronics package 14 and inductive coil 16 are held together by a molded body 18. The molded body 18 may also include suture tabs 20. The molded body narrows to form a strap 22 which surrounds the sclera and holds the molded body 18, inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The inductive coil 16 and molded body 18 are preferably oval shaped. A strap can better support an oval shaped coil.

It should be noted that the entire visual prosthesis is attached to and supported by the sclera. Even though eye motion is useless in the blind, it often continues long after a person has lost their sight. In the embodiment of the present invention it is provided for the entire implantable portion of the prosthesis to be attached to and supported by the sclera. By placing the visual prosthesis under the rectus muscles with the electronics package in an area of fatty tissue between the rectus muscles, eye motion does not cause any flexing which might fatigue, and eventually damage, the visual prosthesis.

Figure 2:
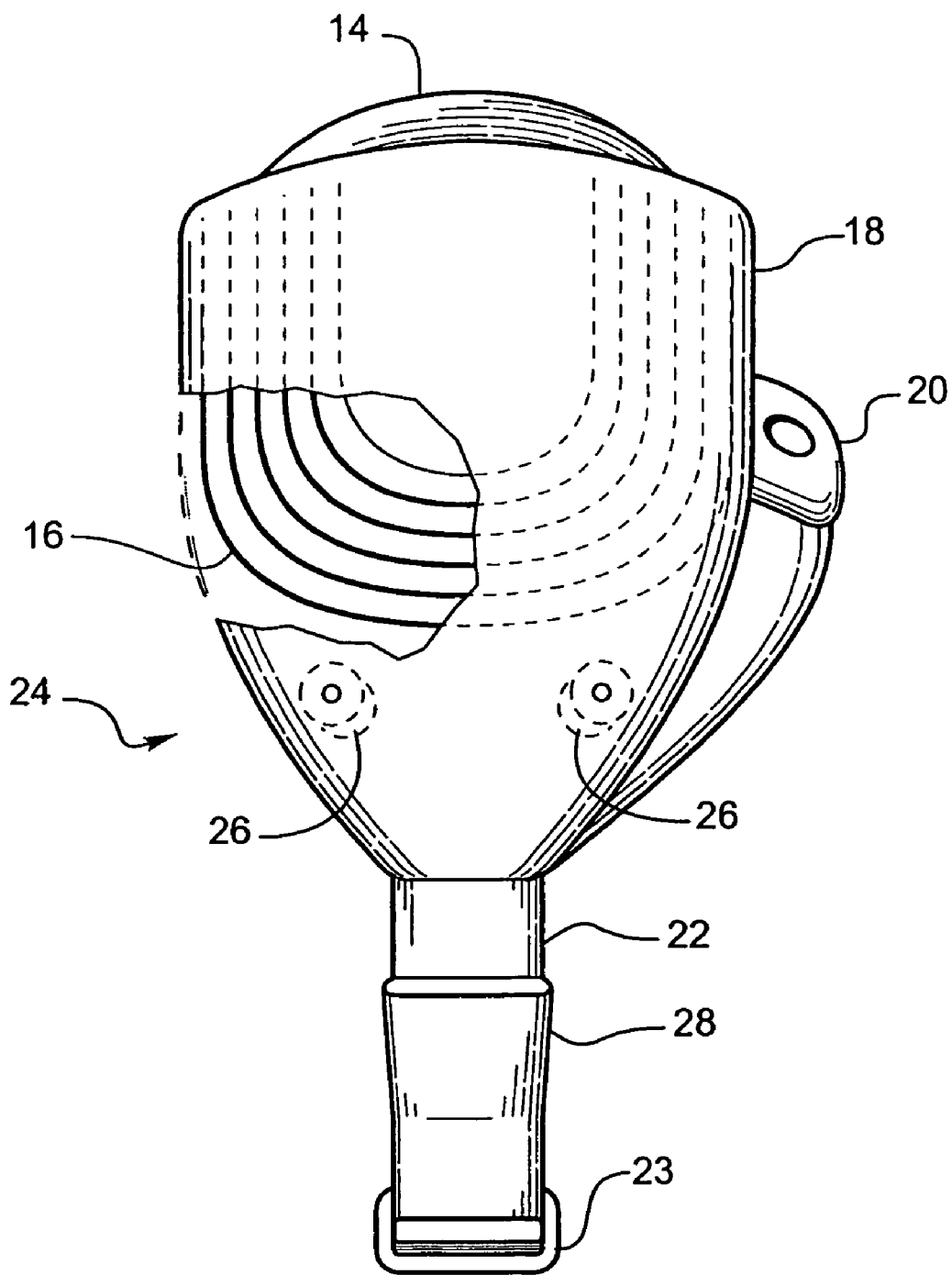
FIG. 2 is an illustration of a perspective side view of an implantable portion of the visual prosthesis showing a fan tail in more detail in accordance with an embodiment of the present invention.

FIG. 2 is an illustration of a side view of an implantable portion of the visual prosthesis showing a fan tail in more detail in accordance with an embodiment of the present invention. When implanting the visual prosthesis, the strap 22 should pass under the eye muscles to surround the sclera. The inductive coil 16 and molded body 18 should also follow the strap under the lateral rectus muscle on the side of the sclera. The implantable portion of the visual prosthesis is very delicate. It is easy to tear the molded body 18 or break wires in the inductive coil 16. In order to allow the molded body 18 to slide smoothly under the lateral rectus muscle, the molded body is shaped in the form of a fan tail 24 on the end opposite the electronics package 14.

Figure 3:
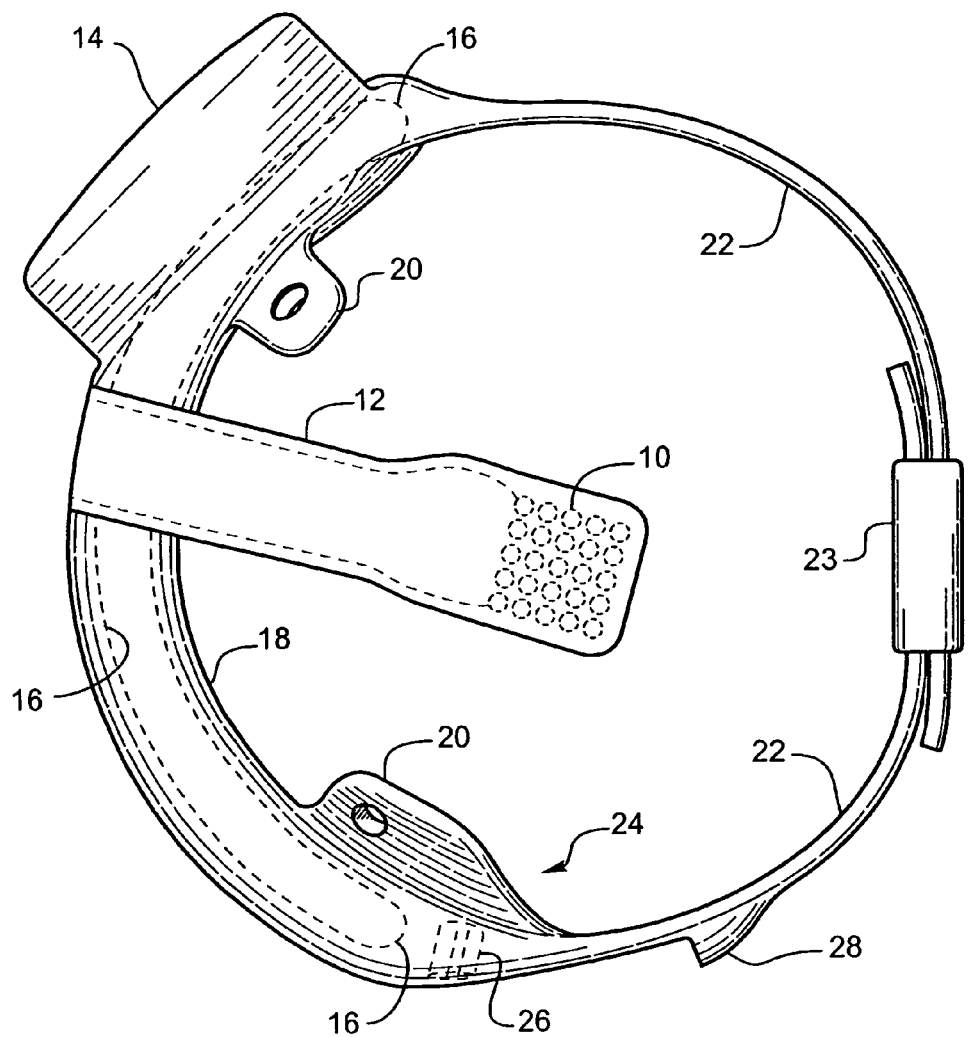
FIG. 3 is an illustration of an perspective edge view of the implantable portion of the visual prosthesis showing a hook for aiding the implantation of the retinal prosthesis.

Referring to FIG. 3, reinforced attachment points 26 are provided to facilitate handling of the visual prosthesis by surgical tools. Preferably, the reinforced attachment points are harder silicone formed around holes through the molded body 18. Further, a hook 28 is molded into the strap 22 just beyond the end of the fan tail 24. A surgical tool can be used against the hook 28 to push the strap 22 under the rectus muscles. The hook 28 is more clearly depicted by the edge view of FIG. 3. The strap 22 is attached to itself by a sleeve 23. The sleeve 23 is a friction device that connects two silicone bands and holds them together with friction. The sleeve 23 is similar to a Watzke sleeve, used with a scleral buckle, and is well known in the art.

In the preferred embodiment, the electrode array 10 and cable 12 are formed layers of a thin polymer film with metal traces sandwiched between the thin polymer films. In such an embodiment, it is advantageous that the film with openings for electrode array 10 be the same film with an opening for connection to the electronics package 14. Therefore, the cable 12 exits the electronics package up away from the fantail 24, folds over itself and exits down toward the fantail 24, before turning at a right angle and piercing the sclera. This allows the same side of the cable to face both the electronics package and the retina. The cable 12 may also include a fantail at the point it is attached to the electronics package 14 and at the point it is attached to the electrode array 10 to reduce any stress on the connections that may be caused by implantation. The cable should exit the molded body 18 toward the front of the eye. The cable should travel above the lateral rectus muscle and pierce the sclera at the pars plana, in front of the retina, so it does not damage the retina. Once inside the eye, the cable 12 can fold back over the retina to properly locate the electrode array 10 on the epiretinal surface.

Figure 4:
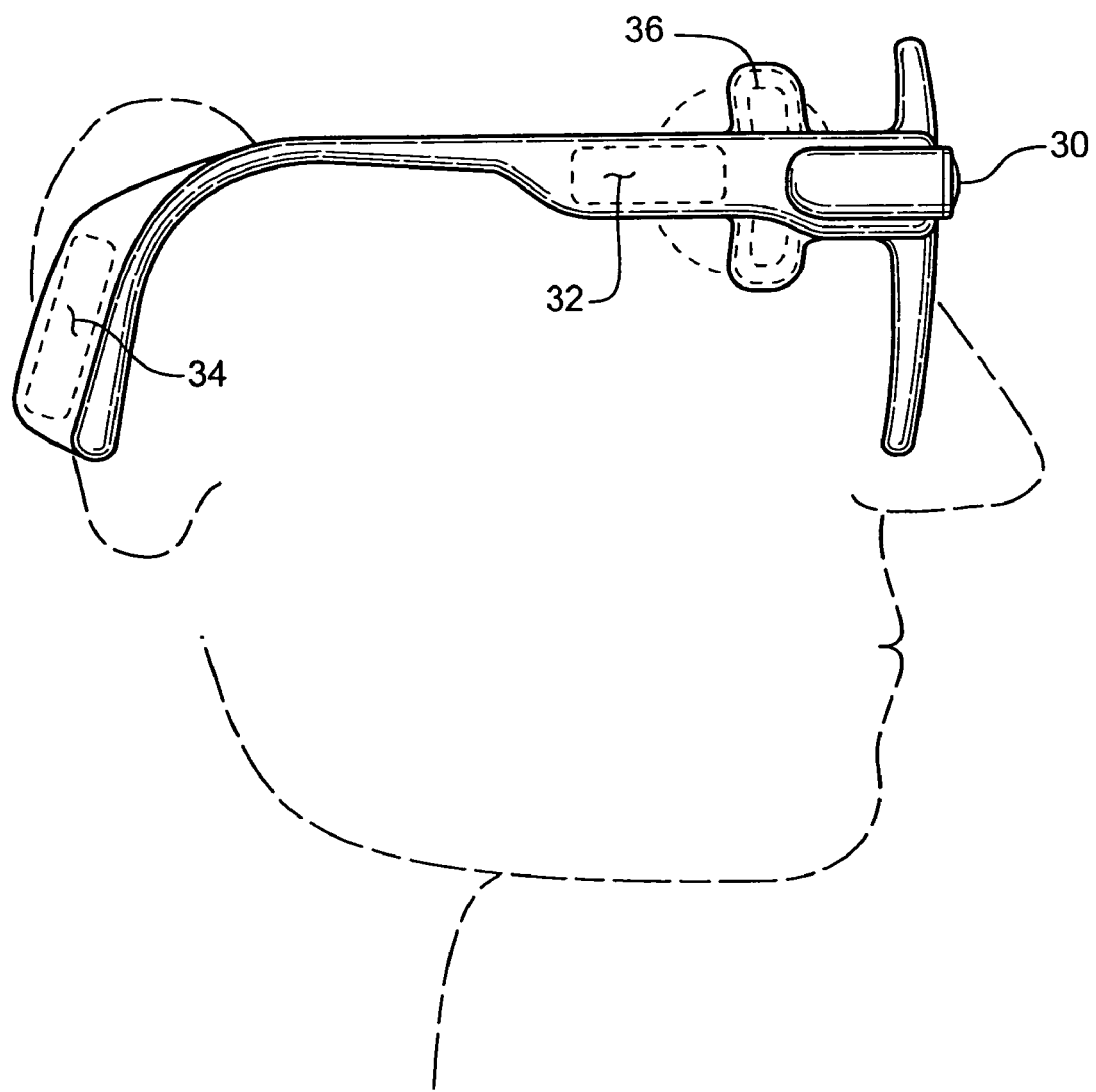
FIG. 4 is an illustration of an external profile view of a user wearing an external portion of a visual prosthesis system.

FIG. 4 is an illustration of an external profile view of a user wearing an external portion of a visual prosthesis system. The external portion may be built into the temple of a pair of glasses. An image processing unit in a form of a camera 30 collects a video image and transmits data to an external electronics package 32. The image processing unit is adapted for detecting features of surrounding objects and generating image signals based on the detected features of the surrounding objects. A battery 34 powers the camera 30, external electronics package 32, and provides power to a primary inductive coil 36. The primary inductive coil 36 sends power and data through the skin and skull to the inductive coil 16. Maximum efficiency is obtained when the primary inductive coil 36 and inductive coil 16 are the same size, shape and as close together as possible.

Figure 5:
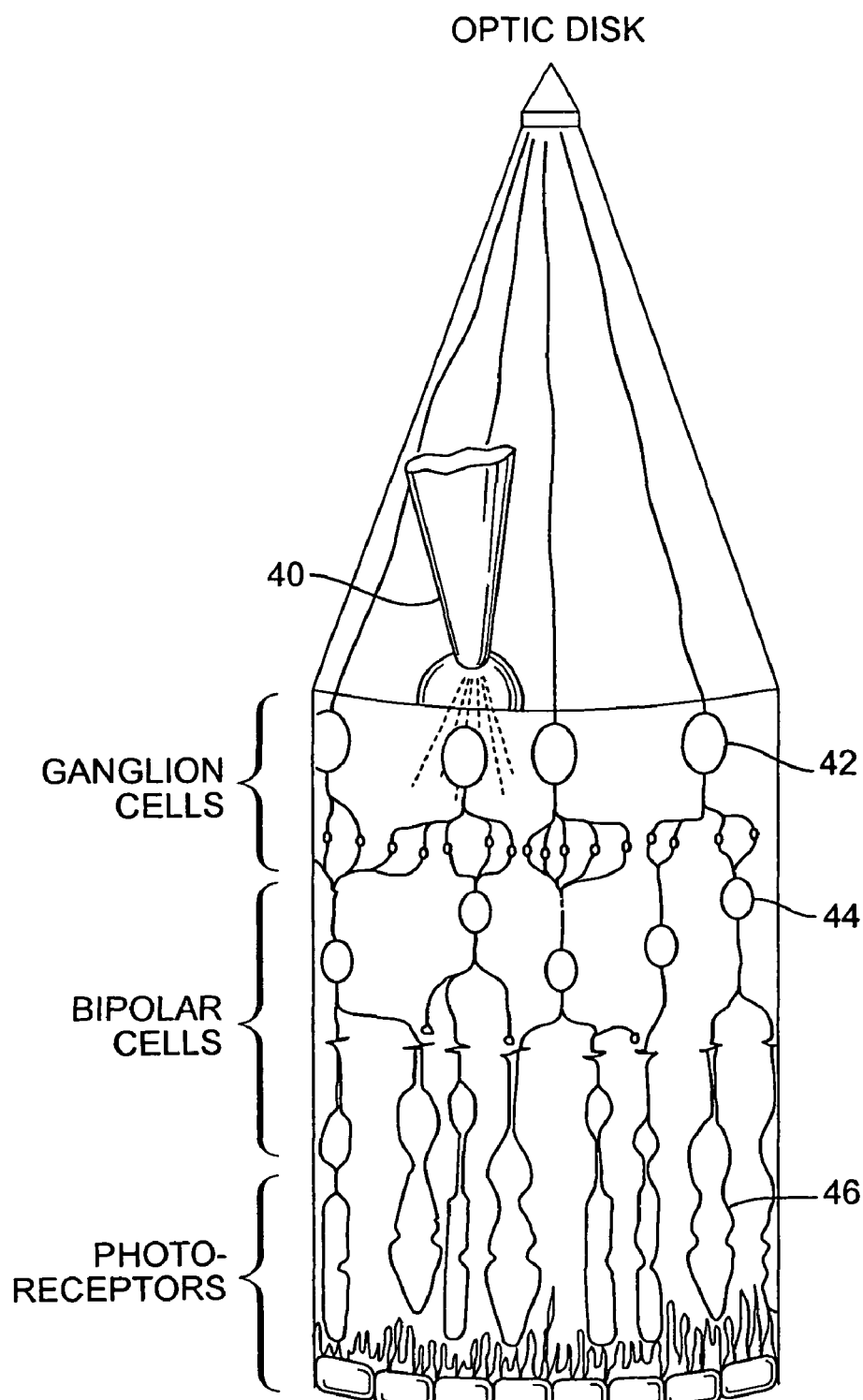
FIG. 5 is an illustration of a schematic representation of a region of retinal tissue being stimulated by an electrode, which is stimulating at least one ganglion cell.

FIG. 5 is an illustration of a schematic representation of a region of retinal tissue being stimulated by an electrode 40, which is stimulating at least one ganglion cell 42, bypassing the photoreceptor cells 46 and bipolar cells 44. In order to restore meaningful vision to blind patients, individual prosthetic electrodes of a visual prosthetic device and system, described above in connection with FIGS. 1-4, should elicit specific spiking patterns in ganglion cells. These patterns should closely resemble the normal light-elicited patterns. In the embodiments of the present invention, it is proposed that a method/stimulus protocol is developed that reliably elicits one ganglion cell spike for each electrical pulse i.e., response for each electrical stimulation imparted on each ganglion cell. The ability to reliably generate individual spikes with high temporal precision allows us to replicate a wide range of spike patterns. Although, the electrical stimulation signals may be different types of signals/waveforms, herein it is contemplated that the stimulation signals are in the form of stimulation pulses.

Broadly, in the embodiments of the present invention, a method, a visual prosthesis and a visual prosthesis system is proposed for stimulating a localized portion of visual tissue. The visual tissue may be at least one visual neuron wherein the visual neuron may be more specifically a retinal neuron. Yet more specifically, as described above, the retinal neuron may be at least one ganglion cell. The method comprises the steps of: a) providing at least one stimulating electrode suitable for placement in proximity to the visual tissue; b) generating at least one stimulation signal, said at least one stimulation signal having a duration of less than about 0.5 milliseconds; and c) applying the at least one stimulation signal to the at least one stimulating electrode, thereby stimulating the localized portion of the visual tissue.

In the experiments conducted, patch clamp recordings were used to measure spiking responses from individual retinal ganglion cells in the flat mounted rabbit retina. Small tipped platinum-iridium epiretinal electrodes were used to deliver biphasic electrical stimulus pulses with stimulation frequencies that ranged from 1-250 Hz. With regard to the stimulation pulses, it is proposed to deliver balanced biphasic current pulses to patients to reduce the biologically harmful product of electrochemical reactions. The pulses are delivered with the cathodic/negative pulse first and then followed by the anodic/positive pulse in order to equalize the cellular charge delivered. In this manner, the biphasic pulse delivers approximately zero net charge. It is proposed that other types of unbalanced pulses may be utilized that would not have harmful biological effects. Moreover, in the present embodiment, it is proposed to stimulate at least one ganglion cell at a frequency greater than about 10 Hz.

To distinguish spiking elicited by direct activation of the ganglion cell from spiking elicited by activation of presynaptic cells, synaptic inputs to ganglion cells were blocked pharmacologically. Light responses and dendritic morphology were used to identify each ganglion cell type. Referring to FIG. 5, the presynaptic cells also referred to as the deeper retinal cells are generally the bipolar cells 44. In a people blinded by retinitis pigmentosa or macular degeneration, the photoreceptors 46 and the bipolar cells 44 may be damaged. Therefore, it is desired to electrically stimulate the ganglion cells 42 directly to achieve a better visual response.

It was realized that long duration electrical pulses of greater than about 1 msec. elicited a single spike within 0.5 msec. of the pulse onset followed by a train of spikes which could persist for more than 50 msec. depending on pulse amplitude levels. Pharmacological blockers of excitatory synaptic input eliminated all but the first spike suggesting that the first spike arises from direct activation of the ganglion cell and all other spikes arise from depolarization due to excitatory input from presynaptic cells.

Experimental evidence suggests that short biphasic pulses preferentially stimulate ganglion cells to the substantial exclusion of direct stimulation of the deeper retinal cells. These short pulses each produce a single spike in ganglion cells within 1 msec. As described, in an embodiment of the present invention, it is proposed to apply at least one stimulation signal, for example, in the form of a biphasic pulse, to a localized portion of visual tissue, wherein the stimulation signal has a duration of less than about 0.5 msec. In further aspects of the embodiment of the present invention, it is proposed to apply stimulation signals having durations of less than about 0.3 msec. preferably less than 0.1 msec. It is further proposed that each stimulation signal, in the form of a stimulation pulse, should have a predetermined substantially constant amplitude.

Short duration pulses elicit one spike per pulse at all stimulation frequencies; therefore they can be used to generate precise temporal patterns of activity in ganglion cells. These patterns can be used to mimic physiologically relevant light evoked responses, e.g., they can replicate the spiking pattern of transient or sustained cells, and also mimic the changes in spike frequency that underlie responses to changing light intensities and contrasts. Furthermore, it is proposed that in addition to light intensities and contrasts, various images may also be mimicked as different spiking patterns of varying spike frequency such that images may be perceived by the patient. This may be accomplished by stimulating at least one ganglion cell with stimulation signals/pulses having varying frequencies corresponding to light-evoked frequency patterns associated with respective images.

Conventionally, the visual perception of low intensity light has been achieved by applying low amplitude pulses, whereas the perception of high intensity light has been achieved by applying high amplitude pulses to the retinal tissue. In contrast, in the embodiments of the present invention, it is proposed that in order to encode the intensity/brightness of an external stimulus, for example, an image, the rate of the pulses provided by the electrodes to the ganglion cells may be varied such that low intensities are represented with low stimulation pulse frequencies and high intensities are represented with high pulse frequencies. The lower and upper bounds of pulse frequency and the relationship between brightness and spike rate should be matched to the normal spiking range of retinal ganglion cells. In other words, is contemplated to stimulate at least one ganglion cell with stimulation signals having varying frequencies corresponding to varying levels of brightness such that the varying frequencies are substantially matched to a spiking range of frequencies of the at least one ganglion cell for perceiving brightness.

In another embodiment of the present invention, it is proposed to stimulate a localized portion of visual tissue, more particularly at least one ganglion cell, at a frequency greater than about 10 Hz notwithstanding the duration of the stimulation signals. It is contemplated that ganglion cell-stimulation at frequencies greater than about 10 Hz elicits one spike per stimulation pulse.

In the experiments conducted, measurements were made of the spiking responses in ganglion cells, the output cells of the retina, using cell-attached patch clamp recordings in the flat mount rabbit retina. Electrical stimulation was delivered by small tipped platinum-iridium (Pt—Ir) electrodes (Impedance: 10-100 k.OMEGA.) and consisted of biphasic (cathodic first), charge balanced square wave current pulses. Amplitudes ranged from 1 to 400 .mu.A and pulse durations ranged from 60 .mu.sec to 6 msec. Light responses were measured continuously during experiments to ensure stability of the recording setup.

FIG. 6A is an illustration of a typical spiking response to a long-pulse electrical stimulation. Large transient currents in the form of sharp large signals 50 were recorded which temporally correlate with the onset 52 and terminations 54 of the individual phases of the stimulus pulse 56. These are electrical 'artifacts' that arise from the application of stimulus pulse and tend to obscure a neural action potential (spike) buried in the trace. By applying tetrodotoxin (TTX), a blocker of neuronal spiking, the response was different but only in the region immediately following the onset of the pulse. Subtracting the TTX response 58 from the control response 60 unmasked a single spike 62 (see FIG. 6B) which was similar in magnitude and kinetics to light evoked spikes. In response to the anodic phase of the stimulus pulse, there was no difference between the control and TTX responses.

FIG. 6B is an illustration of a ganglion cell spike response generated by the long-pulse electrical stimulation shown in FIG. 6A, after subtracting the stimulus artifact recorded during application of TTX 58. FIG. 6A. The spike 62 was elicited immediately after the onset 52 of the pulse 56 as shown in FIG. 6B, suggesting that it was elicited at the leading edge of the pulse 56. In order to further test this observation, the duration of the stimulus pulse was shortened.

FIG. 7A is an illustration of a ganglion cell response when stimulated by a short-stimulus-pulse. FIG. 7A shows the response to a short (0.2 ms) pulse 64 under normal conditions 66 and during the application of TTX 68. As in FIG. 6, subtracting the TTX response from the normal response to eliminate the stimulus artifact reveals the presence of a single spike 70 (see FIG. 7B).

FIG. 7B is an illustration of a single spike response elicited from a ganglion cell when stimulated by a single short-pulse electrical stimulation after subtraction of the electrical stimulation pulse artifact. The response to a short pulse under normal conditions was always triphasic consisting of a large upward and downward deflection followed by a smaller upward deflection. In TTX the response was always biphasic 68 (no second upward deflection). Since TTX eliminates all spiking activity in ganglion cells, the small upward deflection that is eliminated by TTX represents a spiking response from the ganglion cell. In later experiments with short duration pulses the second upward deflection was a reliable marker to indicate that spiking had been elicited.

Figure 8:
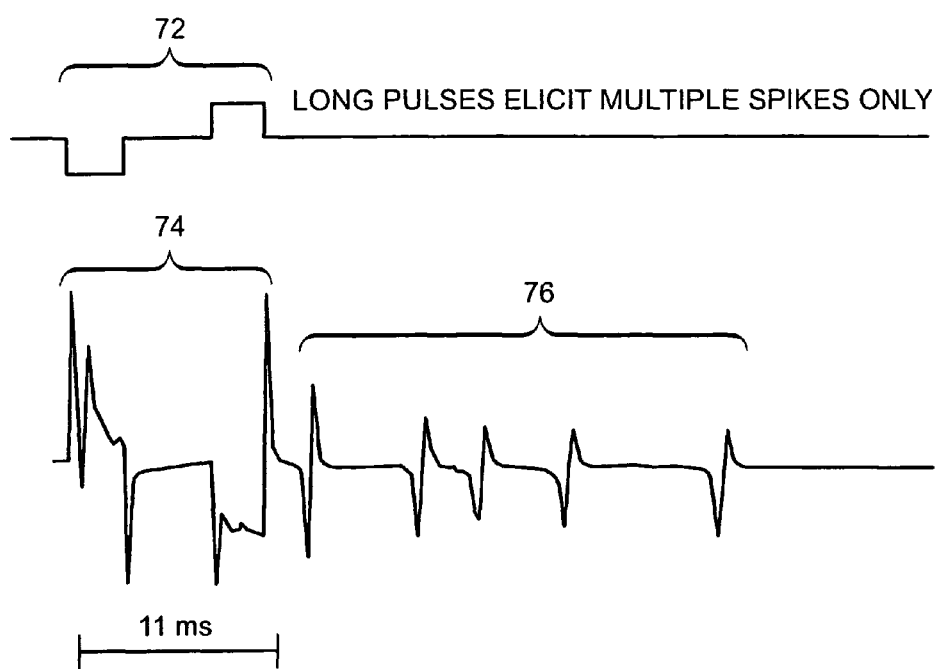
FIG. 8 is an illustration of how the longer-duration stimulation pulses produce early and late phase responses in the ganglion cells.

Longer duration stimulation pulses elicited spiking that occurred after completion of the stimulus pulse, in addition to the spike produced by the leading edge of the stimulus. FIG. 8 illustrates that the longer-duration stimulation pulse produce early and late phase spikes in the ganglion cell. As shown in FIG. 8, the longer-duration stimulation pulse 72 results in an early phase spike response 74 and a late phase spike responses 76. The number and timing of the late phase spike responses was variable and generally increased with increasing stimulation pulse amplitude or duration. Short duration stimulation pulses less than about 0.15 ms did not elicit any of these late phase spike responses. All of the late phase spiking responses were eliminated in the presence of a cocktail of drugs that blocked excitatory synaptic input to ganglion cells, while leaving the initial short latency spike unaffected. This indicates that long-duration stimulation pulses activate presynaptic neurons that release excitatory neurotransmitter which in turn stimulates ganglion cells to produce additional spikes. The early phase single spike response was not eliminated by drugs that block synaptic input from presynaptic cells, indicating that it arises from direct activation of the ganglion cell.

Figure 9A:
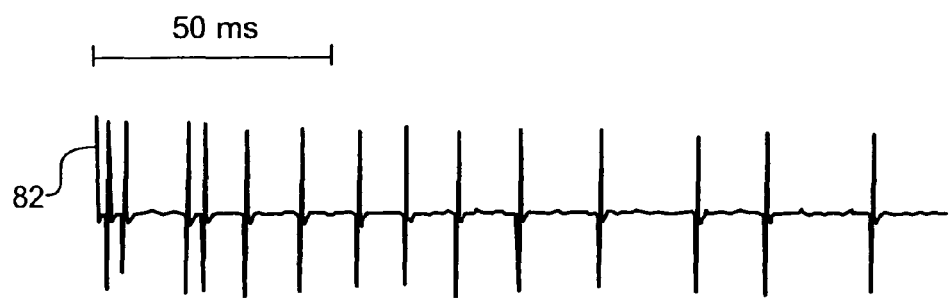
FIG. 9A is an illustration of a light source producing light-elicited spike response pattern.
Figure 9B:
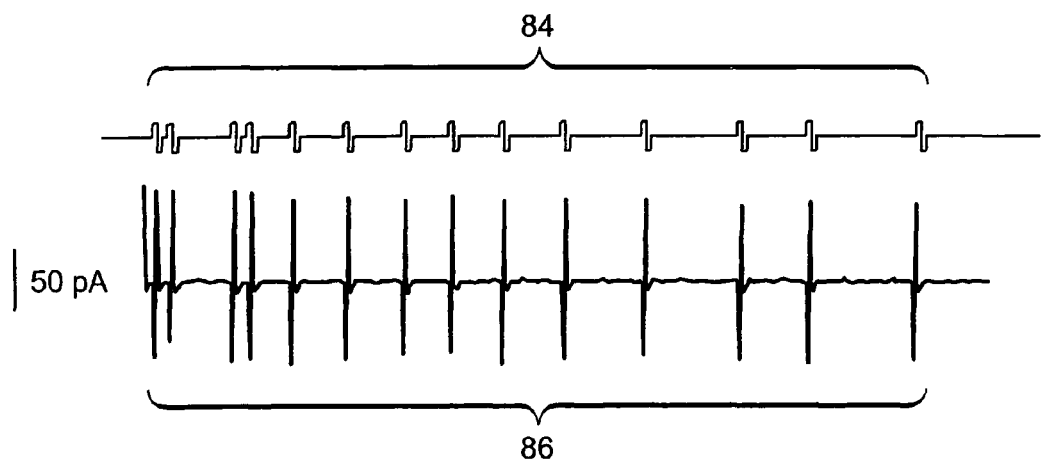
FIG. 9B is an illustration of a short-duration stimulation pulse pattern replicating/mimicking the light-elicited spike response of FIG. 9A.

At higher stimulation frequencies namely, greater than about 10 Hz, short duration stimulation pulses continued to elicit one spike response per stimulation pulse. This was consistent for stimulation frequencies up to 250 Hz. To test if light-elicited spike response patterns could be replicate with short-pulse electrical stimulation, an experiment was conducted. FIG. 9A is an illustration of the spike response pattern 82 produced by a 1 second long pulse of 100 .mu.m square light stimulus. A train of short electrical pulses was then created that had the same temporal pattern as the measured light-evoked spike train 84. FIG. 9B shows that when this pulse pattern was used to stimulate the retina, the resulting spiking pattern 86 accurately replicated/mimicked the pattern produced by the light stimulus.

Figure 10:
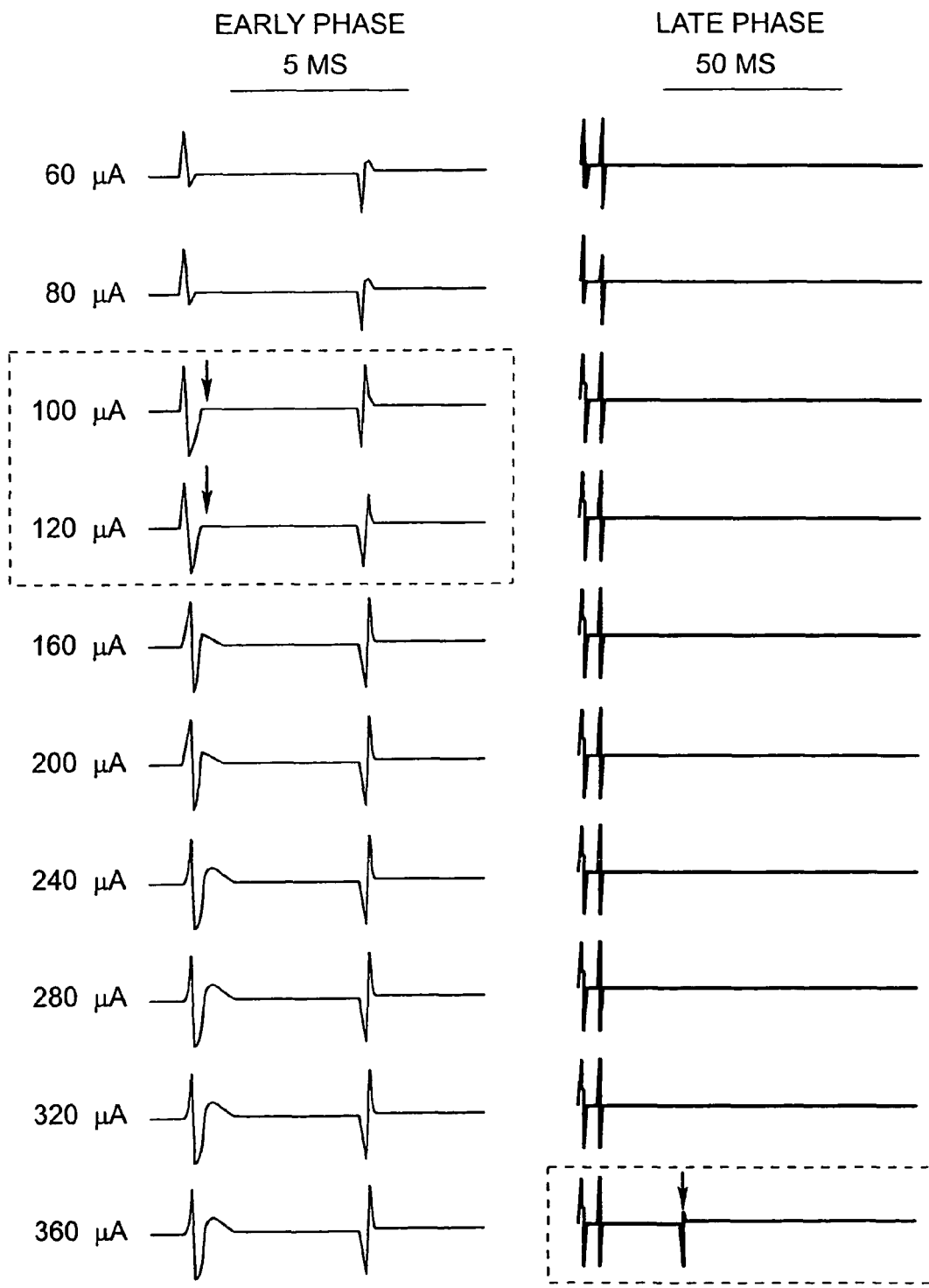
FIG. 10 is an illustration of the spiking responses elicited in a ganglion cell to a short-duration stimulation pulse having varying current amplitudes.

A single spike per pulse could be reliably elicited over a wide range of pulse amplitudes. FIG. 10 is an illustration of the spiking responses elicited in a ganglion cell to a short-duration stimulation pulse having varying current amplitudes. As shown in FIG. 10, pulse amplitudes above 120 .mu.A consistently elicited a single spike response whereas pulse amplitudes above 360 .mu.A elicited late phase spikes which are likely due to activation of presynaptic neurons in addition to the early phase spike.

A stimulus paradigm is developed that elicits one neuronal spike per stimulus pulse and is effective over a wide range of stimulation frequencies and amplitudes. This allows electrical prosthetic devices to mimic the spike patterns sent to the brain during normal vision.

Short pulses are likely to simplify the generation of spatially complex patterns of activity because they activate only ganglion cells. Longer pulses appear to activate bipolar cells. Amacrine cells are also activated, either directly or via synaptic input from bipolar cells. Activation of these presynaptic elements elicits long latency excitation as well as long latency inhibition that can spread over broad spatial regions. The use of short pulses avoids the long latency and broad spatial activity.

Short pulses elicit spiking in ganglion cells using less total charge than long pulses. This may allow for reduced electrode size thereby generating a more focal response.

In addition to encoding intensity information, the embodiments of the present invention could be used to encode other visual attributes with electrical stimulation. Visual information that reaches the brain can be relayed as a pattern of action potentials transmitted down the fibers of the optic nerve. Cells that provide information about specific stimulus attributes, such as color, generally tile the spatial surface of the retina. These cells provide information about the magnitude of any of the attribute that they encode through variations in the rate and timing of their action potentials or spikes. Therefore, the embodiment described here for generating precise patterns of spiking could be used to electrically generate a given stimulus attribute, such as color, by selectively stimulating a particular cell with a predetermined electrical pulse sequence designed to mimic the cell's normal response to that stimulus attribute.

While the invention has been described by means of specific embodiments, it is understood that numerous modifications and variations could be made thereto by those skilled in the art without departing from the spirit and scope of the invention. In particular, one of skill in the art would realize that, while described in terms of retinal stimulation, the principles disclosed are equally applicable to cortical visual stimulation, as well as many other forms of neural stimulation. It is therefore to be understood that within the scope of the claims, the invention may be practiced otherwise than as specifically described herein.

The invention claimed is:

1. A method of stimulating a localized portion of visual tissue comprising the steps of:

providing a two dimensional array of stimulating electrodes suitable for placement in proximity to the visual tissue;

generating a plurality of stimulation signals adapted to mimic neural coding by eliciting a single spike response in at least one visual neuron per stimulation pulse, wherein said generating comprises selecting an amplitude and selecting a frequency of greater than or equal to 1 Hertz and less than or equal to 250 Hertz; and applying said plurality of stimulation signals to said two dimensional array of stimulating electrodes, thereby stimulating the localized portion of the visual tissue and creating perception of light in formed images.

2. The method of claim 1, wherein said plurality of stimulation signals comprise biphasic signals having a negative portion and a positive portion.

3. The method of claim 2, wherein the localized portion of the visual tissue comprises at least one visual neuron.

4. The method of claim 3 wherein the at least one visual neuron is at least one retinal neuron.

5. The method of claim 4, wherein the at least one retinal neuron is at least one ganglion cell.

6. The method of claim 3, wherein said stimulating the localized portion comprises: stimulating at least one ganglion cell to the substantial exclusion of direct stimulation of the deeper retinal cells.

7. The method of claim 6, further comprising; stimulating the at least one ganglion cell with stimulation signals having varying frequencies corresponding to varying levels of brightness.

8. The method of claim 1, wherein said generating further comprises selecting a duration of less than about 1 millisecond for each of the stimulation signals.

* * * * *